US00PP18474P2

(12) United States Plant Patent
Gitzels

(10) Patent No.: US PP18,474 P2
(45) Date of Patent: Feb. 5, 2008

(54) ***DAHLIA* PLANT NAMED 'BALDELMARM'**

(50) Latin Name: *Dahlia pinnata*
Varietal Denomination: Baldelmarm

(75) Inventor: Jeroen Gitzels, Zwaag (NL)

(73) Assignee: Ball Horticultural Company, West Chicago, IL (US)

( * ) Notice: Subject to any disclaimer, the term of this patent is extended or adjusted under 35 U.S.C. 154(b) by 0 days.

(21) Appl. No.: 11/594,614

(22) Filed: Nov. 8, 2006

(51) Int. Cl.
*A01H 5/00* (2006.01)

(52) U.S. Cl. ..... Plt./321
(58) Field of Classification Search ..... Plt./321
See application file for complete search history.

(56) References Cited

U.S. PATENT DOCUMENTS

PP11,701 P * 12/2000 Van Hee ..... Plt./321
PP16,448 P2 * 4/2006 Gitzels ..... Plt./321

OTHER PUBLICATIONS

UPOV ROM GTITM Computer Database, GTI Jouve Retrieval Software 2007/02 Citation for 'Baldelmarm'.*

* cited by examiner

*Primary Examiner*—Wendy Haas
(74) *Attorney, Agent, or Firm*—Audrey Charles

(57) ABSTRACT

A new and distinct cultivar of *Dahlia* plant named 'Baldelmarm', characterized by its double type, medium orange-colored flowers, medium green-colored foliage, and vigorous, semi-upright growth habit.

1 Drawing Sheet

Latin name of genus and species of plant claimed: *Dahlia pinnata.*
Variety denomination: 'Baldelmarm'.

BACKGROUND OF THE INVENTION

The present invention relates to a new and distinct cultivar of *Dahlia* plant botanically known as *Dahlia pinnata* and hereinafter referred to by the cultivar name 'Baldelmarm'.

The new cultivar originated in a controlled breeding program in Rijsenhuot, the Netherlands during June 2003. The objective of the breeding program was the development of *Dahlia* cultivars that are freely flowering with large flowers and a moderately vigorous growth habit.

The new *Dahlia* cultivar is a naturally occurring sport of Dahlia DELICIOUS Lemon Zest 'Baldelemz', U.S. Plant Pat. No. 16,448, characterized by its double type light yellow-colored flowers, medium green-colored foliage, and vigorous, semi-upright growth habit. The new cultivar was discovered as a whole plant and selected on June 2004 in a controlled environment at Rijsenhuot, the Netherlands.

Asexual reproduction of the new cultivar by terminal stem cuttings since June 2004 at Rijsenhuot, the Netherlands, Arroyo Grande, Calif., and West Chicago, Ill. has demonstrated that the new cultivar reproduces true to type with all of the characteristics, as herein described, firmly fixed and retained through successive generations of such asexual propagation.

SUMMARY OF THE INVENTION

The following characteristics of the new cultivar have been repeatedly observed and can be used to distinguish 'Baldelmarm' as a new and distinct cultivar of *Dahlia* plant:

1. Double type, medium orange-colored flowers;
2. Medium green-colored foliage; and
3. Vigorous, semi-upright growth habit.

Plants of the new cultivar differ from plants of the parent primarily in flower color.

Of the many commercially available *Dahlia* cultivars known to the inventor, the most similar in comparison to the new cultivar is DAHLIETTA Rachel 'Dapaor', U.S. Plant Pat. No. 11,701. However, in side by side comparisons, plants of the new cultivar differ from plants of 'Dapaor' in the following characteristics:

1. Plants of the new cultivar are taller than plants of 'Dapaor';
2. Plants of the new cultivar have a growth habit different from plants of 'Dapaor'; and
3. Plants of the new cultivar have flower color that is slightly different from plants of 'Dapaor'.

BRIEF DESCRIPTION OF THE PHOTOGRAPHS

The accompanying photographs show, as nearly true as it is reasonably possible to make the same in color illustrations of this type, typical flower and foliage characteristics of the new cultivar. Colors in the photographs differ slightly from the color values cited in the detailed description, which accurately describes the colors of 'Baldelmarm'. The plants were grown in 4.5 inch pots for 8 weeks in a greenhouse at West Chicago, Ill.

DETAILED BOTANICAL DESCRIPTION

Figure 1:
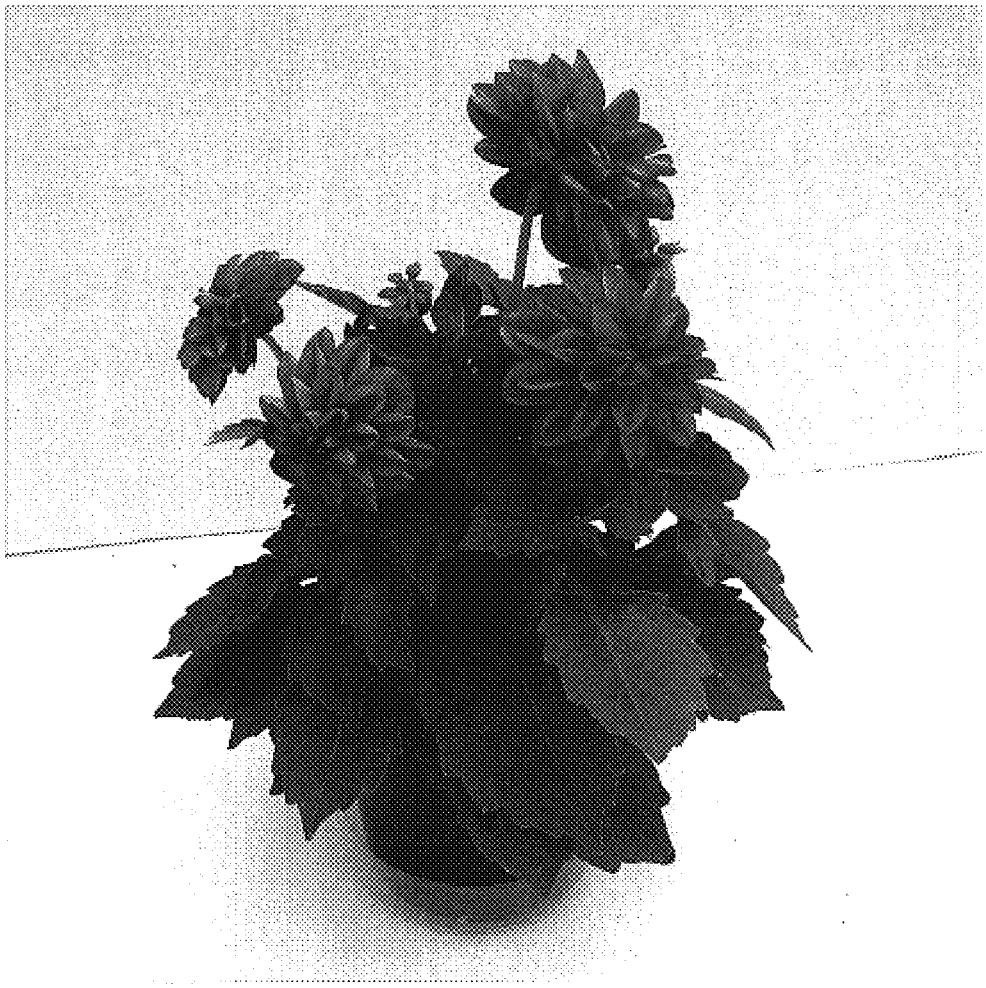
FIG. 1 illustrates a side view of the overall growth and flowering habit of 'Baldelmarm'.
Figure 2:
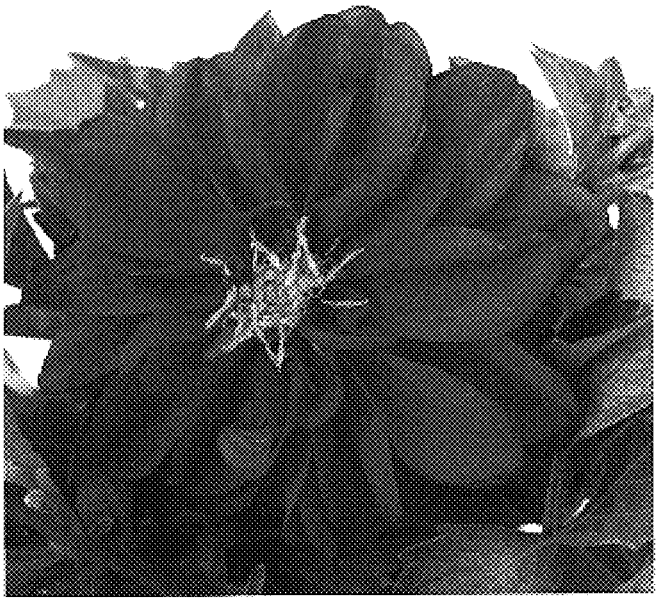
FIG. 2 illustrates a close-up view of an individual inflorescence of 'Baldelmarm' with all of the ray florets and disc florets open.

The new cultivar has not been observed under all possible environmental conditions to date. Accordingly, it is possible that the phenotype may vary somewhat with variations in the environment, such as temperature, light intensity, and day length, without, however, any variance in genotype.

The chart used in the identification of colors described herein is The R.H.S. Colour Chart of The Royal Horticultural Society, London, England, 2001 edition, except where general color terms of ordinary significance are used. The color values were determined on May 17, 2006 between 9:00 a.m. and 11:00 a.m. under natural light conditions in West Chicago, Ill.

The following descriptions and measurements describe plants produced from cuttings taken from stock plants and grown in a glass-covered greenhouse under conditions comparable to those used in commercial practice. The plants were grown at West Chicago, Ill. in 4.5 inch pots for 8 weeks utilizing a soilless growth medium. Greenhouse temperatures were maintained at approximately 70° F. to 77° F. (21° C. to 25° C.) during the day and approximately 65° F. to 68° F. (18° C. to 20° C.) during the night. Greenhouse light levels of 2,500 footcandles to 6,000 footcandles were maintained during the day.

Botanical classification: *Dahlia pinnata* cultivar Baldelmarm.

Parentage:

*Parent.*—Delicious™ Lemon Zest 'Baldelemz', U.S. Plant Pat. No. 16,448.

Propagation:

*Type cutting.*—Terminal stem.

*Time to initiate roots.*—Approximately 7 to 10 days.

*Time to produce a rooted cutting.*—Approximately 28 to 32 days.

*Root description.*—Fine, fibrous.

*Rooting habit.*—Freely branching.

*Tuber formation.*—Will form under short day conditions of at least 13 to 14 hours of darkness.

Plant description:

*Commercial crop time.*—Approximately 8 to 10 weeks.

*Growth habit and general appearance.*—Vigorous, semi-upright.

*Size.*—Height from soil level to top of plant plane: Approximately 23.3 cm. Height from soil level to top of foliage: Approximately 15.7 cm. Width: Approximately 19.2 cm.

*Branch.*—Quantity per plant: Approximately 7. Strength: Strong. Length: Approximately 12.3 cm. Diameter: Approximately 3.6 mm. Texture: Glabrous. Color: 144C. Length of central internode: Approximately 2.8 cm.

Foliage description:

*General description.*—Quantity of leaves per lateral branch: Approximately 7. Type: Simple and compound. Quantity of leaflets per compound leaf: Approximately 3. Fragrance: None. Arrangement: Opposite. Aspect: Petiole is at an acute angle to stem and mature leaf blade is perpendicular to stem. Shape of leaf and leaflet: Ovate. Margin of leaf and leaflet: Widely serrate, ciliate. Apex of leaf and leaflet: Acuminate: Base of leaf and leaflet: Attenuate. Venation pattern: Pinnate.

*Simple leaf.*—Length: Approximately 6.8 cm. Width: Approximately 4.3 cm. Texture of upper surface: Densely pubescent on venation. Texture of lower surface: Sparsely pubescent on venation. Color of upper surface: Closest to 137A with venation of 146B. Color of lower surface: Between 191C and 191B with venation of 146C. Length of petiole: Approximately 2.6 cm. Diameter of petiole: Approximately 3.0 mm. Texture of upper surface of petiole: Sparsely pubescent. Texture of lower surface of petiole: Glabrous. Color of upper surface of petiole: 144B. Color of lower surface of petiole: 144C.

*Mature trifolate leaf.*—Length of mature trifoliate leaf: Approximately 10.2 cm. Width of mature trifoliate leaf: Approximately 8.1 cm. Length of terminal leaflet: Approximately 5.7 cm. Width of terminal leaflet: Approximately 3.8 cm. Length of lateral leaflet: Approximately 4.3 cm. Width of lateral leaflet: Approximately 2.7 cm. Texture of upper surface: Densely pubescent on venation. Texture of lower surface: Sparsely pubescent on venation. Color of upper surface: Closest to 137A with venation of 146B. Color of lower surface: Between 191C and 191B with venation of 146C. Length of petiole of mature trifolate leaf: Approximately 1.0 cm. Diameter of petiole of mature trifoliate leaf: Approximately 2.8 mm. Texture of upper surface of petiole of mature trifolate leaf: Sparsely pubescent. Texture of lower surface of petiole of mature trifolate leaf: Glabrous. Color of upper surface of petiole of mature trifoliate leaf: 144B. Color of lower surface of petiole of mature trifoliate leaf: 144C. Length of rachis: Approximately 3.1 cm. Diameter of rachis: Approximately 3.4 mm. Texture of upper surface of rachis: Sparsely pubescent. Texture of lower surface of rachis: Glabrous. Color of upper surface of rachis: 144B. Color of lower surface of rachis: 144C.

Flowering description:

*Flowering habit.*—'Baldelmarm' is freely flowering under outdoor growing conditions with substantially continuous blooming from spring through autumn and year-round in greenhouse environment.

*Lastingness of individual inflorescence on the plant.*—Approximately 4 weeks.

Inflorescence description:

*General description.*—Type: Composite, double. Persistent. Shape: Hemispherical when ray florets are fully open. Aspect: Facing outward. Flower arrangement: Terminal, arising from leaf axils on strong peduncles positioned over the foliage. Disc and ray florets arranged acropetally on a capitulum. Quantity per plant: Approximately 3. Diameter: Approximately 7.9 cm. Depth: Approximately 4.5 cm. Fragrance: None.

*Peduncle.*—Strength: Strong. Aspect: Erect. Length: Approximately 9.1 cm. Diameter: Approximately 3.0 mm. Texture: Glabrous. Color: 144B.

*Bud.*—Rate of bud opening: Approximately 2 weeks. Shape: Oblate. Depth at first color: Approximately 1.2 cm. Diameter at first color: Approximately 1.7 cm. Texture at first color: Glabrous. Color: Outer surface of phyllaries is 154B with base of 143A and petal background of 34B.

*Ray florets.*—Quantity per inflorescence: Approximately 87. Arrangement: Imbricate, in multiple whorls. Aspect: Cupped. Shape: Ovate. Margin: Entire. Apex: Rounded. Base: Fused into a short corolla tube. Appearance: Velvety. Length: Approximately 3.5 cm. Width: Approximately 2.0 cm. Texture of upper surface: Glabrous. Texture of lower surface: Sparsely pubescent, ribbed. Color of upper surface when first open: 44A. Color of lower surface when first open: 44B. Color of upper surface when fully open: 33A transitioning to 22A at base. Color of lower surface when fully open: 32B with ribs and base of 22B.

*Disc florets.*—Quantity per inflorescence: Approximately 42. Arrangement: Massed in center of inflorescence. Aspect: Erect. Shape: Tubular. Margin: Entire. Apex: 5 acute tips. Base: Fused. Length: Approximately 1.5 cm. Diameter at apex: Approximately 2.8 mm. Diameter at base: Approximately 1.0 mm. Texture: Glabrous. Color when fully open: 21B, translucent.

*Disc.*—Diameter: Approximately 1.8 cm.

*Receptacle.*—Diameter at base: Approximately 1.1 cm. Depth: Approximately 3.3 mm. Color: 151C.

*Outer phyllaries.*—Quantity: Approximately 6. Aspect: Flat. Shape: Obovate. Margin: Entire. Apex: Acute. Base: Truncate. Length: Approximately 1.2 cm. Width: Approximately 5.0 mm. Texture of upper and lower surfaces: Glabrous. Color of upper and lower surfaces: 137A.

*Inner phyllaries.*—Quantity: Approximately 1 per floret. Shape: Linear, slightly overlapping. Margin: Entire. Apex: Broadly acute. Base: Truncate. Length of outermost: Approximately 1.8 cm. Width of outermost: Approximately 7.4 mm. Length of innermost: Approximately 1.1 cm. Width of innermost: Approximately 2.0 mm. Texture of upper and lower surfaces of all inner phyllaries: Glabrous. Color of upper and lower surfaces: 154B, translucent with a base of 143A for outermost.

*Reproductive organs.*—Androecium: On disc florets. Stamen quantity: 5 per floret. Anther shape: Linear. Anther length: Approximately 4.0 mm. Anther color: 21B, translucent. Pollen amount: Abundant. Pollen color: 24A. Gynoecium: On disc and ray florets. Pistil length: Approximately 1.5 cm. Stigma shape: 2 branches. Stigma length: Approximately 3.6 mm. Stigma color: 23A. Style length: Approximately 8.0 mm. Style color: 151D. Ovary diameter: Approximately 2.0 mm. Ovary color: 1D.

Seed and fruit production: Neither seed nor fruit production has been observed.

Disease and pest resistance: Resistance to pathogens and pests common to *Dahlia* has not been observed.

What is claimed is:

1. A new and distinct cultivar of *Dahlia* plant named 'Baldelmarm', substantially as herein shown and described.

* * * * *